(12) United States Patent
Xu et al.

(10) Patent No.: US 11,353,442 B2
(45) Date of Patent: Jun. 7, 2022

(54) PHYSICAL SIMULATION EXPERIMENTAL DEVICE AND METHOD FOR WATER INVASION AND DRAINAGE GAS RECOVERY IN GAS RESERVOIRS

(71) Applicant: PetroChina Company Limited, Beijing (CN)

(72) Inventors: Xuan Xu, Beijing (CN); Xizhe Li, Beijing (CN); Yong Hu, Beijing (CN); Yongxin Han, Beijing (CN); Yunsheng Wei, Beijing (CN); Yujin Wan, Beijing (CN); Chunyan Jiao, Beijing (CN); Zhenhua Guo, Beijing (CN); Haifa Tang, Beijing (CN); Weigang Huang, Beijing (CN); Guangzhen Chu, Beijing (CN); Yunhe Su, Beijing (CN)

(73) Assignee: PETROCHINA COMPANY LIMITED, Beijing (CN)

( * ) Notice: Subject to any disclaimer, the term of this patent is extended or adjusted under 35 U.S.C. 154(b) by 458 days.

(21) Appl. No.: 16/663,616

(22) Filed: Oct. 25, 2019

(65) Prior Publication Data

US 2020/0132656 A1 Apr. 30, 2020

(30) Foreign Application Priority Data

Oct. 25, 2018 (CN) .......................... 201811249342.1

(51) Int. Cl.
*G01N 33/24* (2006.01)
*G01V 99/00* (2009.01)

(52) U.S. Cl.
CPC ............. *G01N 33/24* (2013.01); *G01V 99/00* (2013.01)

(58) Field of Classification Search
CPC ................................. G01N 33/24; G01V 99/00
See application file for complete search history.

(56) References Cited

U.S. PATENT DOCUMENTS

2004/0211252 A1* 10/2004 Lenormand ........ G01N 15/0826
73/152.05
2021/0150933 A1* 5/2021 Hu .......................... E21B 43/00

FOREIGN PATENT DOCUMENTS

CN 201671605 U 12/2010
CN 102944666 A 2/2013
(Continued)

OTHER PUBLICATIONS

Hu Yong, et al., The experimental study of water invasion mechanism in fracture and the influence on the development of gas reservoir, Natural Gas Geoscience, vol. 27, No. 5.
(Continued)

*Primary Examiner* — Andrew Schechter
*Assistant Examiner* — Kaleria Knox
(74) *Attorney, Agent, or Firm* — The Dobrusin Law Firm, P.C.; Bryan S. Lemanski

(57) ABSTRACT

The invention provides a physical simulation experimental device and method for water invasion and drainage gas recovery in gas reservoir, and the experimental device includes: a heterogeneous reservoir model having a first core holder, a second core holder, a third core holder and a fourth core holder, wherein the third core holder is connected between the first core holder and the second core holder, and the fourth core holder is connected between an outlet end of the first core holder and an outlet end of the second core holder; a gas injection mechanism having a gas injection bottle and a gas injection cylinder; a water body simulation mechanism having a water storage tank and a water injection pump. The invention can simulate and reveal different drainage gas recovery modes, timings, scales and their influences on the recovery ratio of the gas reservoir.

20 Claims, 1 Drawing Sheet

(56) References Cited

FOREIGN PATENT DOCUMENTS

| | | | |
|---|---|---|---|
| CN | 203308392 U | 11/2013 | |
| CN | 105239973 A | 1/2016 | |
| CN | 106285645 A | 1/2017 | |
| CN | 107478807 A * | 12/2017 | ............ G01N 33/24 |
| CN | 107478807 A | 12/2017 | |
| CN | 107905769 A | 4/2018 | |
| CN | 108344853 A | 7/2018 | |
| CN | 108505979 A | 9/2018 | |
| CN | 102830214 A | 12/2019 | |
| EP | 1167948 A1 | 1/2002 | |
| KR | 102010068090 | 6/2010 | |

OTHER PUBLICATIONS

Wang Lu, et al., Experiments on gas supply capability of commingled production in a fracture-cavity carbonate gas reservoir, Petroleum Exploration and Development, vol. 44, No. 5.
First Office Action and Search Report dated Dec. 28, 2020 for counterpart Chinese patent application No. 201811249342.1, along with EN translation.
The Physical Experiment and Numerical Model of Water Invasion to the Gas Reservoir, Science Technology and Engineering, vol. 14, No. 10, pp. 191-194.
The experimental study of water invasion mechanism in fracture and the influence on the development of gas reservoir, Natural Gas Geoscience, vol. 27,No. 5, pp. 910-917.
Chinese Search Report dated Sep. 27, 2018.

\* cited by examiner

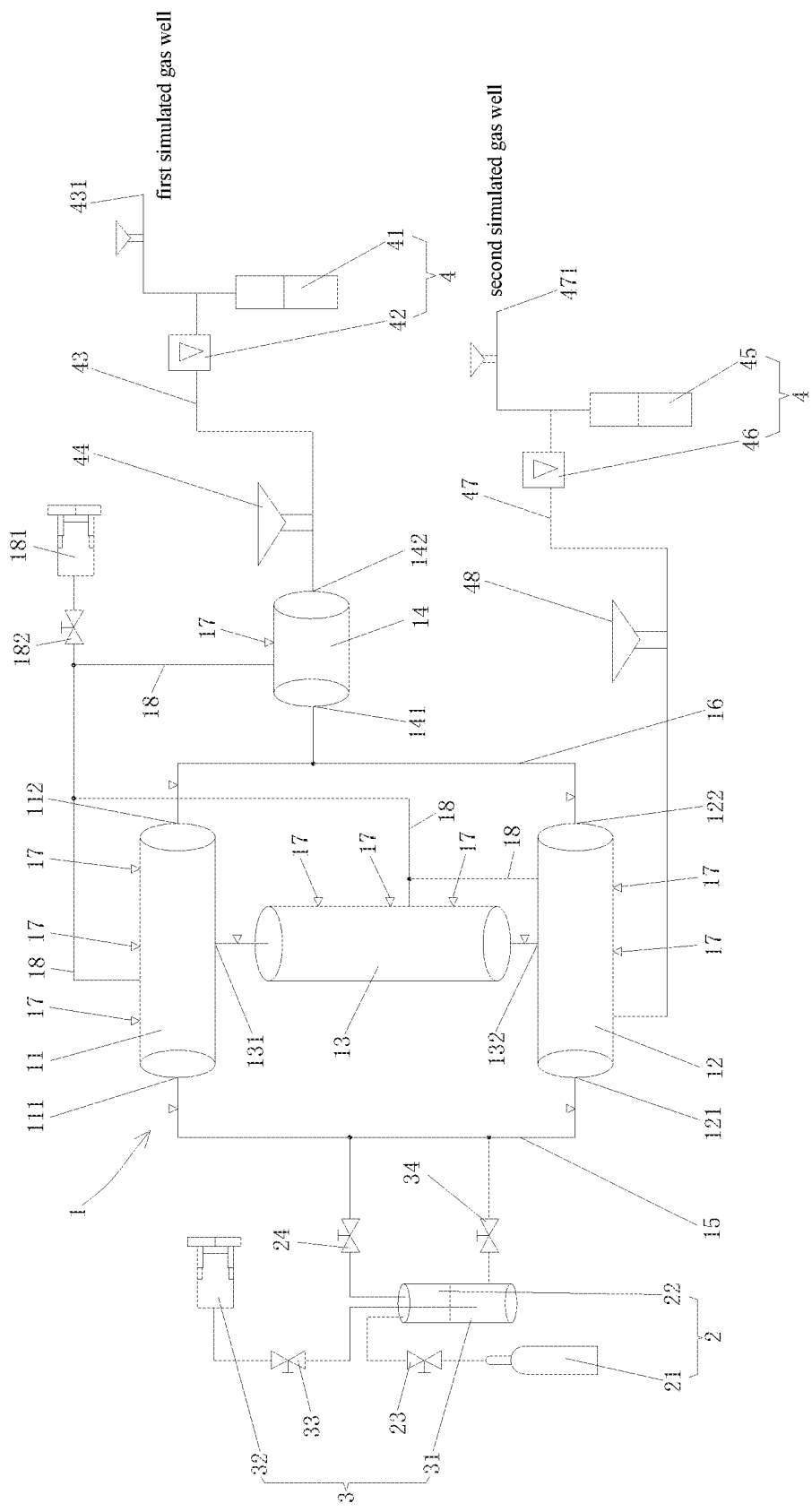

12
PHYSICAL SIMULATION EXPERIMENTAL DEVICE AND METHOD FOR WATER INVASION AND DRAINAGE GAS RECOVERY IN GAS RESERVOIRS

CROSS-REFERENCE TO RELATED APPLICATION

This application claims priority to Chinese Patent Application No. 201811249342.1, filed on Oct. 25, 2018, which is hereby incorporated by reference in its entirety.

TECHNICAL FIELD

The invention relates to the experimental technical field of simulating reservoir forming and mining in the field of oil and gas exploration and development, and in particular to a physical simulation experimental device and method for a water invasion and drainage gas recovery in a gas reservoir.

BACKGROUND

With the development of gas reservoirs, especially after entering the middle and late period of development, the edge water and bottom water adjacent to the gas layer will gradually invade into a gas area, and the water will invade into a gas-producing channel to block the gas-producing channel, divide the reservoir, accelerate the decline, and reduce a recovery ratio of the gas reservoir. On the other hand, for the gas reservoir where water invasion has occurred, the production of gas wells is greatly reduced after water production, and it is difficult to carry water by the gas well's own energy, so it is often difficult to maintain production. At this time, it is necessary to rely on a drainage gas recovery process to maintain production. However, different types of reservoirs have different water invasion modes, different water invasion mechanisms, and different water control countermeasures. Therefore, it is necessary to carry out physical simulation experiment research on water invasion law and drainage gas recovery countermeasures in gas reservoirs, so as to prevent the unreasonable invasion of edge and bottom water, formulate water control countermeasures, and provide theoretical support for carrying out drainage gas recovery measures.

Existing physical simulation experimental technologies mainly focus on the physical simulation method of the water invasion into the gas reservoir, mainly for the study of the characteristics of the water invasion and the production dynamics, and there is basically no physical simulation experimental method for the drainage gas recovery in gas reservoirs, not to mention continuous and unified physical simulation experimental study on the process of continuous occurrence of water invasion and drainage gas recovery in the gas reservoir development. In addition, the existing physical simulation experiment of water invasion in the gas reservoirs can only obtain curves of gas and water production produced by gas wells, and can not obtain the dynamic changes of pressure and water saturation profiles at different positions inside the gas reservoirs, so that it is impossible to reflect the cutting effect of water invasion on the gas reservoir and the distribution of remaining reserves during the water invasion, and it is impossible to reflect the influence of drainage gas recovery measures on the re-production of reserves.

SUMMARY

The purpose of the present invention is to provide a physical simulation experimental device and a method for a water invasion and drainage gas recovery in a gas reservoir, which can continuously carry out the physical simulation experiment for water invasion and drainage gas recovery in gas reservoirs, clarify influences of the water invasion on cutting effect of the gas reservoir and the distribution of remaining reserves, simulate and reveal different drainage gas recovery modes, timings, scales and their influences on the recovery ratio of the gas reservoir.

The above purpose of the present invention can be achieved by adopting the following technical solutions:

The invention provides a physical simulation experimental device for a water invasion and drainage gas recovery in a gas reservoir, wherein the device comprises:

a heterogeneous reservoir model having a first core holder and a second core holder, wherein an inlet end of the first core holder is connected to an inlet end of the second core holder by an inlet pipeline, an outlet end of the first core holder is connected to an outlet end of the second core holder by an outlet pipeline, a third core holder is connected between a middle portion of the first core holder and a middle portion of the second core holder, and a fourth core holder is connected to the outlet pipeline;

a gas injection mechanism having a gas injection bottle and a gas injection cylinder connected to the gas injection bottle, and the gas injection cylinder being connected to the inlet pipeline; and a water body simulation mechanism having a water storage tank and a water injection pump connected to the water storage tank, the water storage tank being connected to the inlet pipeline.

The present invention also provides a physical simulation experimental method for a water invasion and drainage gas recovery in a gas reservoir, which adopts the physical simulation experimental device for the water invasion and drainage gas recovery in the gas reservoir as described above, and the physical simulation experimental method for the water invasion and drainage gas recovery in the gas reservoir comprises the following steps of:

step S1: selecting a fractured rock sample which has a natural fracture or in which an artificial fracture of a rock sample is made, or selecting a matrix rock sample having no fracture, to form an experimental rock sample;

step S2: putting the experimental rock sample into the first core holder, the second core holder, the third core holder and the fourth core holder, respectively; and step S3: starting the gas injection mechanism and the water body simulation mechanism to inject gas and water body into the heterogeneous reservoir model to simulate the gas reservoir environment.

The physical simulation experimental device and the method for the water invasion and drainage gas recovery in the gas reservoir according to the present invention has the following characteristics and advantages: in combination with the actual problem of water invasion and drainage gas recovery in the production process, the physical simulation experimental device and method for water invasion and drainage gas recovery in gas reservoir are established in the present invention. In consideration of various geological factors and production measures such as reservoir having different physical properties, scales of different water bodies, different production distributions and the like, an experiment of water invasion in a gas reservoir is carried out to make a study on main controlling factors and the dynamic law of water invasion, to clarify the influence of water invasion on the cutting effect of gas reservoir and the distribution of remaining reserves, and provide a basis for the adjustment of development policy and well network deployment. The physical simulation experiment of drainage gas recovery is carried out continuously after water production in gas wells, to simulate and reveal different drainage gas recovery modes, timings, scales and their influences on the recovery ratio of the gas reservoir, and provide a theoretical support for preventing unreasonable invasion of edge and bottom water and formulating water control countermeasures. The invention has great significance on studying multiphase seepage, water invasion and water production laws of oil and gas reservoirs, production of remaining reserves, water control countermeasures, and the like.

BRIEF DESCRIPTION OF THE DRAWINGS

In order to more clearly explain the technical solution in the embodiments of the invention, drawings that need to be used in description of the embodiments will be simply introduced below, obviously the drawings in the following description are merely some examples of the invention, for persons ordinarily skilled in the art, it is also possible to obtain other drawings according to these drawings without making creative efforts.

FIG. 1 is a schematic diagram of a structure of a physical simulation experimental device for a water invasion and drainage gas recovery in a gas reservoir according to the present invention.

DETAILED DESCRIPTION

Hereinafter the technical solution in the embodiments of the present invention will be described clearly and integrally in combination with the accompanying drawings in the embodiments of the present invention, and obviously the described embodiments are merely part of the embodiments, not all of the embodiments. Based on the embodiments of the present invention, all other embodiments that are obtained by persons skilled in the art without making creative efforts fall within the protection scope of the present invention.

Embodiment 1

As shown in FIG. 1, the invention provides a physical simulation experimental device for a water invasion and drainage gas recovery in a gas reservoir, and the physical simulation experimental device comprises:

a heterogeneous reservoir model 1 having a first core holder 11 and a second core holder 12, wherein an inlet end 111 of the first core holder 11 is connected to an inlet end 121 of the second core holder 12 through an inlet pipeline 15, an outlet end 112 of the first core holder 11 is connected to an outlet end 122 of the second core holder 12 through an outlet pipeline 16, a third core holder 13 is connected between a middle portion of the first core holder 11 and a middle portion of the second core holder 12, and a fourth core holder 14 is connected to the outlet pipeline 16;

a gas injection mechanism 2 having a gas injection bottle 21 and a gas injection cylinder 22 connected to the gas injection bottle 21, wherein the gas injection cylinder 22 is connected to the inlet pipeline 15; and a water body simulation mechanism 3 having a water storage tank 31 and a water injection pump 32 connected to the water storage tank 31, wherein the water storage tank 31 is connected to the inlet pipeline 15.

Specifically, the heterogeneous reservoir model 1 is a main body of an experimental device and consists of a plurality of core holders, in the embodiment, four core holders are provided in total, i.e., a first core holder 11, a second core holder 12, a third core holder 13, and a fourth core holder 14. Herein, an inlet pipeline 15 is connected between the inlet end 111 of the first core holder 11 and the inlet end 121 of the second core holder 12, and an outlet pipeline 16 is connected between the outlet end 112 of the first core holder 11 and the outlet end 122 of the second core holder 12, an inlet end 131 of the third core holder 13 and an outlet end 132 of the third core holder 13 are connected to a side wall of the first core holder 11 and a side wall of the second core holder 12, respectively, and an inlet end 141 of the fourth core holder 14 is connected to the outlet pipeline 16.

The heterogeneous reservoir model can simulate different gas reservoir types and reservoir conditions by core combination of different reservoir types and physical properties. For example, a fractured rock sample which has a natural fracture or in which artificial fracture of a rock sample is made may be selected according to the experimental requirements; or a matrix rock sample having no fracture may also be selected according to the experimental requirements. Different core combinations are formed by placing different types of rock samples in different core holders. In the present invention, the permeability and the degree of fracture development of a fractured rock sample or a matrix rock sample may be selected according to actual geological models and experimental purposes according to the experimental requirements, which are not limited herein.

The gas injection mechanism 2 is used to inject a high-pressure gas into the heterogeneous reservoir model 1 to simulate the original pressure conditions of the gas reservoir. The gas injection mechanism 2 has a gas injection bottle 21 and a gas injection cylinder 22, and in the embodiment, the gas injection bottle 21 is a high-pressure gas bottle, and a first gas injection valve 23 is connected between the gas injection bottle 21 and the gas injection cylinder 22, a second gas injection valve 24 is connected between the gas injection cylinder 22 and the inlet pipeline 15, and the first gas injection valve 23 and the second gas injection valve 24 are opened to achieve the purpose of injecting high-pressure gas into the heterogeneous reservoir model 1 through the gas injection bottle 21.

The water body simulation mechanism 3 is used for injecting a water body into the heterogeneous reservoir model 1 to simulate a water body environment in the gas reservoir, and the water body may be an infinite water body or a limited water body. The water body simulation mechanism 3 has a water storage tank 31 and a water injection pump 32, a first water injection valve 33 is connected between the water storage tank 31 and the water injection pump 32, and a second water injection valve 34 is connected between the water storage tank 31 and the inlet pipeline 15. By opening the first water injection valve 33 and the second water injection valve 34, the purpose of injecting water into the heterogeneous reservoir model 1 can be achieved.

In an embodiment of the present invention, the gas injection cylinder 22 of the above gas injection mechanism 2 and the water storage tank 31 of the water body simulation mechanism 3 may be combined into an intermediate container in which a movable piston may be provided, and the piston separates the intermediate container into the water storage tank 31 located at a lower portion of the intermediate container and the gas injection cylinder 22 located at an upper portion of the intermediate container.

In the present invention, the first core holder 11, the second core holder 12, the third core holder 13 and the fourth core holder 14 are respectively provided with a plurality of measuring holes in each of which a pressure and resistivity probe 17 can be connected, so as to realize the measurement of pressure and saturation inside the core during the experiment. In the course of the experiment, the residual reserve distribution and water invasion dynamics can be described in real time by measuring the pressure and saturation inside the rock sample. The pressure and resistivity probe 17 comprises a pressure sensor and a resistivity probe, wherein pressure sensors may be respectively connected in the measuring holes of the first core holder 11, the second core holder 12, the third core holder 13 and the fourth core holder 14. These pressure sensors form a pressure testing mechanism of the present invention, and the pressure sensors can monitor and reflect the change of the residual pressure and water saturation of the gas reservoir in real time, so as to obtain the distribution of residual gas that cannot be detected in the actual production process, the higher residual pressure indicates that no gas is produced in the core, and the lower residual pressure indicates that the gas has been produced in larger quantities. In addition, a plurality of resistivity probes, which form the saturation testing mechanism of the present invention, may be connected in the measuring holes of the first core holder 11, the second core holder 12, the third core holder 13, and the fourth core holder 14, respectively. These resistivity probes can measure resistivity values of the rock samples in each of the core holders in real time, and then convert the resistivity values into water saturation according to the Archie formula. In the embodiment, the pressure and resistivity probe 17 can be connected to an external automatic detection software that can automatically record the pressure and resistivity values at different positions during the experiment, the minimum recording interval is 10 seconds/time. These resistivity probes can monitor and reflect the change of water saturation in the gas reservoir in real time, and can obtain the dynamic process of water invasion that cannot be detected in the actual production process through the change of water saturation, for example, the water saturation of water-invaded cores rises during the advance of the water invasion frontier. The pressure and resistivity probe 17 of the present invention enables the gas and water conditions inside the gas reservoir to be monitored, which is of great significance for studying the gas reservoir development and drainage gas recovery mechanism, gas and water product rules.

In the present invention, each of the first core holder 11, the second core holder 12, the third core hold 13, and the fourth core holder 14 is connected to a confining pressure pipeline 18, the confining pressure pipeline 18 can be connected to a confining pressure pump 181, and a confining pressure valve 182 is provided between the confining pressure pump 181 and the confining pressure pipelines 18. The confining pressure valve 182 is opened to provide confining pressure for the rock sample in each core holder through the confining pressure pump 181 and the confining pressure pipelines 18 to simulate the core overlying pressure condition. In the present invention, the confining pressure can be up to 70 Mpa, and the confining pressure must always be higher than the pore pressure 3 MPa~70 MPa of the rock sample.

In the embodiment of the present invention, the physical simulation experimental device for water invasion and drainage gas recovery in gas reservoir further comprises: at least one gas-water production and metering mechanism 4 connected to a heterogeneous reservoir model 1, the gas-water production and metering mechanism 4 includes a gas-water separation meter and a flow controller, and the gas-water production and metering mechanism 4 is used to produce and accurately meter the flow rates of gas and water.

In a feasible embodiment, a gas-water production and metering mechanism 4 is connected to the first core holder 11, the gas-water production and metering mechanism 4 includes a gas-water separation meter 41 and a flow controller 42, the gas-water separation meter 41 is connected to an outlet end 142 of the fourth core holder 14 through a first outlet water pipeline 43 which is provided with the flow controller 42 and a first back-pressure valve 44. Herein, the gas-water separation meter 41 can separate the produced gas and water, and meanwhile can meter the contents of the separated gas and water, and the flow controller 42 can control and meter the gas-water yield in the first outlet water pipeline 43.

Furthermore, in another feasible embodiment, another gas-water production and metering mechanism 4 is connected to the second core holder, the gas-water production and metering mechanism 4 includes a gas-water separation meter 45 and a flow controller 46, the gas-water separation meter 45 is connected to the second core holder 12 through a second outlet water pipeline 47, e.g., be connected into the measuring hole of the second core holder 12, and the second outlet water pipeline 47 is provided with the flow controller 46 and a second back-pressure valve 48. The gas-water separation meter 45 can separate the produced gas and water, and meanwhile can meter the contents of the separated gas and water, and the flow controller 46 can control and meter the gas-water yield in the second outlet water pipeline 47.

Furthermore, the third core holder 13 and/or the fourth core holder 14 may also be connected to the gas-water production and metering mechanism 4, respectively, so as to meter the gas and water flows produced in the rock sample in the corresponding core holder according to the experimental requirements.

The physical simulation experimental device for a water invasion and drainage gas recovery in a gas reservoir according to the present invention can continuously carry out the physical simulation experiment for the water invasion and drainage gas recovery in the gas reservoirs, and monitor the pressure and water saturation values at different positions inside the gas reservoirs in real time, so as to clarify influences of the water invasion on cutting effect of the gas reservoir and the distribution of remaining reserves, simulate and reveal different drainage gas recovery modes, timings, scales and their influence on the recovery ratio of the gas reservoir.

The steps of performing various experiments by the physical simulation experimental device for the water invasion and drainage gas recovery in the gas reservoir according to the present invention are described in detail below:

Physical Simulation Experiment for Water Invasion and Drainage Gas Recovery in Gas Reservoirs Before the experiment, it is necessary to simulate the gas reservoir environment of the physical simulation experimental device for a water invasion and drainage gas recovery in the gas reservoir, and specifically, to select a fractured rock sample which has a natural fracture or in which an artificial fracture of a rock sample is made, or select a matrix rock sample having no fracture, to form an experimental rock sample; putting the experimental rock sample into the first core holder 11, the second core holder 12, the third core holder 13 and the fourth core holder 14, respectively; then the gas injection mechanism 2 is started to inject gas into the heterogeneous reservoir model 1, to communicate the water body simulation mechanism 3 with the first core holder 11 and the second core holder 12 to simulate the gas reservoir with the water body. The above steps simulate the gas reservoir environment having the water body. After that, the physical simulation experiment for water invasion and drainage gas recovery in the gas reservoir is performed, and the detailed description is as follows:

1. During a first stage of the experiment, the process of gradual invasion of the edge and bottom water adjacent to the gas layer into the gas area during gas reservoir development process is simulated, the gas-producing channel is blocked, the reservoir is divided, the decline is accelerated, and the recovery ratio of the gas reservoir is reduced. The mechanism of water invasion is studied, and influence of the water invasion on the cutting effect of the gas reservoir and the distribution of remaining reserves is clarified.

In this stage, the gas reservoir with water body is simulated, and in the process of exploitation, the water body invades into the gas reservoir along the high permeability reservoir such as fracture, blocks and cuts the reservoir, resulting in descending of gas well production and decrease of the recovery ratio. Specifically:

A fractured rock sample is placed in the first core holder 11 and the second core holder 12 of the heterogeneous reservoir model 1, respectively, a matrix rock sample is placed in the third core holder 13, and a rock sample may not be placed or a fractured rock sample/a matrix rock sample may be placed in the fourth core holder 14.

First, the second water injection valve 34 is opened to communicate the water tank 31 with the first core holder 11 and the second core holder 12.

The first back-pressure valve 44 is opened to set an outlet pressure of the first outlet water pipeline 43, and the gas or water flows out from the outlet 431 of the first outlet water pipeline 43 to simulate the production of the first gas well, and the second back-pressure valve 48 is in a closed state.

The instantaneous gas and water flow and the accumulated gas and water flow during the experiment are recorded by the flow controller 42 and the gas-water separation meter 41 on the first outlet water pipeline 43, respectively.

In addition, the pressure and resistivity values of different parts of the gas reservoir during the experiment are recorded respectively by a plurality of pressure and resistivity probes 17 arranged at the side and both ends of each core holder, to reflect the change of residual pressure and water saturation in different parts of the gas reservoir, so as to display the residual reserve distribution and water invasion dynamics.

During the water invasion process of the gas reservoir, the water flows along the fractured rock sample in the first core holder 11 and the fractured rock sample in the second core hold 12 intrudes into the matrix rock sample in the third core holder 13 around the fracture, which may cause certain closing and cutting effects on the matrix rock sample, resulting in that the residual gas in the matrix rock sample in the third core holder 13 cannot be produced. In this process, the permeability of the fractured rock sample in the first core holder 11, the permeability of the fractured rock sample in the second core holder 12, and the permeability of the matrix rock sample in the third core holder 13 have significant effects on water invasion and reserves production.

Furthermore, to simulate the effect on development of the fracture size of the fractured rock sample in the first core holder 11 and the fractured rock sample in the second core holder 12 and the degree of permeability matching with the matrix rock sample in the third core holder 13, in the experiment, the following ways can be used to perform the simulation respectively by:

simulating the influences of different fracture sizes: adjusting the permeability of the fractured rock sample in the first core holder 11 and the fractured rock sample in the second core holder 12, selecting a combination of fractured rock sample of different fracture sizes (i.e., different permeabilities) and the matrix rock samples, and simulating influences of the fracture sizes and the permeabilities of matrix rock sample on water invasion and production of remaining reserves. For example, the permeability of the fractured rock sample in the first core holder 11 is taken as 100 mD, the permeability of the matrix rock sample in the third core holder 13 is taken as 1.5 mD, and the permeability of the fractured rock sample in the second core holder 12 is taken as 1000 mD. During the experiment, the change law of the pressure and saturation of the fractured rock sample in the first core holder 11, the fractured rock sample in the second core holder 12, and the matrix rock sample in the third core holder 13 are recorded, so as to obtain the reserve size and water invasion range at different positions of the gas reservoir.

The influences of different matrix sizes are simulated: by adjusting the length of the matrix rock sample in the third core holder 13, the gas supply ranges of different matrix rock samples are simulated. For example, the length of the matrix rock sample in the third core holder 13 can be set to 10 cm, 30 cm or 50 cm respectively, the lengths of the matrix rock sample in the third core holder 13 are different, and the pressures and saturations at different positions during the experiment are different, so as to simulate the influences of the range of the matrix reservoir on the water invasion and the production of remaining reserves.

The influences of different degree of fracture penetration are simulated. During water invasion, the degree of fracture penetration (a ratio of length of the fracture reservoir to length of total reservoirs) has an important influence on water invasion velocity, gas well recovery and reserve production of the gas reservoir. In the experiment, simulation can be performed by: adjusting the length of the rock sample in the fourth core holder 14 to simulate the influence of the degree of fracture penetration on the water invasion of the gas reservoir and the production of reserves. For example, when the length of the rock sample in the fourth core holder 14 is set to 0 cm, i.e., the water body directly communicates with the first gas well through the fractured rock sample penetrating through the first core holder 11 and the fractured rock sample penetrating through the second core holder 12 (the degree of penetration corresponds to 100%), and once the gas well starts production, the water body very easily invades into the first gas well along the fracture, thereby causing the gas in the matrix rock sample in the third core holder 13 to be closed without time to be produced. This process is monitored by the change law of pressure and saturation at different locations of the gas reservoir. When the length of the rock sample in the fourth core holder 14 is set to be the same as the length of the fractured rock sample penetrating through the first core holder 11 and the length of the fractured rock sample in the second core holder 12, it corresponds to a simulated gas reservoir fracture penetration degree of 50%. In the production process, there will be great difference in water invasion velocity and reserve production degree.

The influences of different water body sizes are simulated by: adjusting the volume of the water storage tank 31, which can simulate the influence of different water body sizes on the water invasion and reserves production of gas reservoirs. During the experiment, the first water injection valve 33 is opened, the water storage tank 31 is directly connected to a constant pressure water injection pump 32, and the water body energy is supplemented by the water injection pump 32 during the water invasion, so that the water body pressure in the water storage tank 31 can be kept constant and the infinite constant pressure water body can be simulated. By closing the first water injection valve 33 and adjusting the amount of water in the water storage tank 31, different water body sizes can be simulated, and specifically in the experiment, the size of the water storage tank 31 can be set according to the ratio of the volume of water body to the pore volume of the reservoir, for example, 10 times of water body or 30 times of water body.

The first back-pressure valve 44 and the flow controller 42 can be used to control the outlet pressure and gas water flow of the first gas well, respectively, to simulate the influences of different waste pressures and production distributions on gas reservoir production. For example, if the pore pressure of the initially saturated gas of the core reservoir is 30 MPa, the outlet pressure can be set to 20 MPa, 10 MPa, 2 Map or 0.1 MPa. Outlet flow may be set to 100 mL/min or 1000 mL/min. Pressure and flow can be designed according to specific gas reservoir parameters and experimental requirements.

2. The second stage of the experiment is to simulate the gas reservoir where water invasion has taken place, based on the process of preventing and controlling the unreasonable invasion of edge and bottom water by a drainage gas recovery process, and to study the influence mechanism and law of different timings for drainage gas recovery and drainage measures on the enhanced recovery ratio of the gas reservoir.

In the actual development process, a variety of measures and countermeasures will be taken for drainage gas recovery after water invasion. The main methods include: (1) reducing bottom hole flow pressure and increasing production pressure difference of the first gas well through drainage measures of the first gas well, thereby realizing drainage gas recovery of the first gas well; (2) co-drainage of multiple wells, that is, a second gas well is provided at a position closer to the water body in a direction of incoming water and a water invasion path, and the water is produced in advance through the second gas well. Due to the large amount of water production in the second gas well, the energy of the water body is reduced, so that the risk of further invasion of the water body into the fractured rock sample in the first core holder 11 and into the fractured rock sample in the second core holder 12 is greatly reduced. In the experiment, simulation is performed by the follow methods respectively:

First gas well drainage gas recovery simulation: in the initial stage of development, a certain abandonment pressure (for example, 5 MPa, 3 MPa) is set to the first gas well through the first back-pressure valve 44 to perform production, and at a certain stage, the water body begins to invade, and the output of the first gas well decreases. At this time, at the current outlet pressure of the first gas well, it is difficult for the first gas well to maintain production. By adjusting the outlet pressure of the first gas well by the first back-pressure valve 44, the outlet pressure of the first gas well is reduced (for example, 2 MPa or atmospheric pressure). The drainage of the first gas well is simulated to reduce the flow pressure and increase the production differential pressure so as to simulate the process of reproducing gas from the first gas well. During the experiment, the change of gas and water production and the change of pressure and water saturation at different locations in the first gas well are observed and recorded, and the mechanism and law of different drainage gas recovery timing and measures on gas reservoir reserves production and the recovery ratio are studied.

The first gas well and the second gas well cooperate in drainage gas recovery simulation: after the first gas well performs production for a certain time, the direction of water body invasion can be judged by the pressure and resistivity probe 17, and the second gas well can be newly deployed at a position close to the water body. For example, in the experiment, if it is found after monitoring that the water saturation of the fractured rock sample in the second core holder 12 rises, drainage may be performed on the side of the fractured rock sample in the second core holder 12 that is close to the water body specifically by opening the second back-pressure valve 48 to cause the second gas well to start production, at which time the invaded water will flow out through the second gas well, and the gas water flow rate of the second gas well is metered respectively. After the large amount of water production in the second gas well, the energy of the water storage tank 31 may be reduced, so that the risk of further invasion of the water body into the fractured rock sample in the first core holder 11 and into the fractured rock sample in the second core holder 12 is greatly reduced. In that process, a variety of different drainage measures can be simulated and their influence on water invasion and reserves production can be studied by.

simulating different drainage timings: by controlling the timing of opening the second back-pressure valve 48, to simulate the influence of the second gas well cooperative drainage timing on the production. For example, the first gas well and the second gas well are opened for production at the same time at the early stage of development; the second gas well is opened for production at the end of the first gas well stable production stage at the early stage of development; and the second gas well is opened for production after the first gas well production greatly decreases at the late stage of development. The influence of different drainage timing on water invasion and reserves production can be detected by the pressure and resistivity probe 17 at different positions of the gas reservoir.

Simulation of different drainage locations: different locations of drainage wells deployed in production also have great influence on the drainage gas recovery effect, which can be simulated by setting the second gas well at different locations in the rock sample. The second gas well is led out through a measuring hole on the side of the core holder, which may be disposed at different parts of the fractured rock sample in the first core holder 11 or the fractured rock sample in the second core holder 12, and may also be provided on the matrix rock sample in the third core holder 13 to simulate different drainage locations during the development of the gas reservoir.

Simulation of different drainage strengths: different outlet pressure or gas and water production of the second gas well can be controlled by the second back-pressure valve 48 and the second flow controller 46, thereby to simulate the influence of different drainage strengths on water invasion and reserve production, for example, the outlet pressure of the second gas well may be set to 5 MPa or 3 MPa.

The physical simulation experimental device for water invasion and drainage gas recovery in gas reservoir according to the present invention has the following characteristics and advantages:

(1) In the invention, the technical blank that there is no experiment on continuous simulation of the water invasion and the drainage gas recovery process of the gas reservoir is filled, and provides an experimental device that can continuously carry out the physical simulation experiment for water invasion and drainage gas recovery in gas reservoirs. In the invention, the pressure and water saturation values of different positions inside the gas reservoir can be monitored in real time during the experimental process, and then the effect of water invasion on the cutting action of the gas reservoir and the distribution of the remaining reserves are studied, to simulate and reveal different drainage gas recovery modes, timing, scale and their influence on the recovery ratio of the gas reservoir.

(2) In the invention, the pressure and the water saturation at different positions of the gas reservoir during the development experiment of the gas reservoir can be measured in real time by connecting the pressure and the resistivity probes by providing measuring hole on the side of each core holder. The pressure parameter measurement is very important for studying the division and closing mechanism of water invasion to the reservoir, the distribution of residual reserves and the process of producing residual reserves after drainage. The water saturation parameter is very important for studying the water invasion mechanism of gas reservoir, such as the range of water invasion, the advancing velocity of front edge of water invasion, and the change of water saturation in the process of drainage gas recovery, and the like.

(3) The present invention provides a specific simulation method for various water invasion conditions and drainage gas recovery measures by deeply studying the geological conditions and production conditions and by optimizing the combination and design of experimental models and experimental conditions and the like. In the invention, various water invasion conditions and influence factors can be simultaneously simulated, for example, the influence of different fracture and matrix scales is simulated; the influence of different fracture penetration degree is simulated; the influence of different water body scales is simulated; and the influence of different waste pressure and production is simulated. In addition, the invention continuously carries out the drainage experiment after the water invasion experiment, can simultaneously simulate the drainage gas recovery of a single gas well; simulate the cooperative drainage gas recovery of different gas wells; and simulates different drainage timings, drainage positions and drainage scales, etc. The experimental device can be used to simulate and study different geological and production conditions, different water invasion mechanism and drainage measures in a comprehensive and systematic way.

(4) In the invention, the water invasion and drainage gas recovery experiment of the gas reservoir under the high pressure condition can be simulate, and the water body and the reservoir state under the formation condition can be restored, so that the experimental process and the result are more accurate and more accord with the production reality.

Embodiment 2

As shown in FIG. 1, the present invention also provides a physical simulation experimental method for water invasion and drainage gas recovery in gas reservoir, which is implemented by adopting the physical simulation experimental device for water invasion and drainage gas recovery in gas reservoir as described in the Embodiment 1, the physical simulation experimental method for water invasion and drainage gas recovery in gas reservoir comprising the following steps of:

step S1: selecting a fractured rock sample which has a natural fracture or in which an artificial fracture of a rock sample is made, or selecting a matrix rock sample having no fracture, to form an experimental rock sample;

step S2: putting the experimental rock sample into the first core holder 11, the second core holder 12, the third core holder 13 and the fourth core holder 14, respectively;

step S3: starting the gas injection mechanism 2 and the water body simulation mechanism 3 to inject gas and water body into the heterogeneous reservoir model 1 to simulate the gas reservoir environment.

According to an embodiment of the present invention, a step S4 is performed after the step S3: the fourth core holder 14 of the heterogeneous reservoir model 1 is connected with gas-water production and metering mechanism 4 to form a first simulated gas well, the gas-water production and metering mechanism 4 includes a gas-water separation meter 41 and a flow controller 42; the gas or water body in the heterogeneous reservoir model 1 is discharged through the gas-water production and metering mechanism 4 to simulate a fracture water invasion process of the gas reservoir.

In an embodiment, experimental rock samples having different permeabilities are placed in the first core holder 11, the second core holder 12, the third core holder 13, and the fourth core holder 14, respectively, to simulate the influences of different fracture sizes.

In an embodiment, experimental rock samples having different lengths are placed in the first core holder 11, the second core holder 12, the third core holder 13 and the fourth core holder 14, respectively, to simulate the influence of different matrix scales and different degrees of fracture penetration.

In an embodiment, the heterogeneous reservoir model 1 is supplemented with water body by a water body simulation mechanism 3, to simulate the effects of different water body sizes.

In an embodiment, the gas-water production and metering mechanism 4 of the first simulated gas well is provided with a first back-pressure valve 44, the outlet pressure and gas flow rate of the first simulated gas well are controlled by the first back-pressure valve 44 and a flow controller, to simulate the effects of different waste pressure and production allocation.

According to an embodiment of the present invention, the gas-water production and metering mechanism 4 of the first simulated gas well is provided with a first back-pressure valve 44 through which the waste pressure of the heterogeneous reservoir model 1 is set and then to perform production. The water body in the heterogeneous reservoir model 1 begins to invade into the experimental rock samples, and by adjusting the first back-pressure valve 44, the outlet pressure of the first simulated gas well is reduced to simulate the process of drainage gas recovery of the first simulated gas well.

In an embodiment, the second core holder 12 of the heterogeneous reservoir model 1 is connected with the gas-water production and metering mechanism 4 to form a second simulated gas well, and a process of cooperative drainage gas recovery is simulated though the second simulated gas well and the first simulated gas well.

In an embodiment, the gas-water production and metering mechanism 4 of the second simulated gas well is provided with a second back-pressure valve 48, and the opening timing of the second back-pressure valve 48 is controlled to simulate different drainage timings.

In an embodiment, the gas-water production and metering mechanism 4 of the second simulated gas well can be connected to the outlet end of the second core holder 12 or to the side wall of the second core holder 12 to simulate different drainage locations.

In an embodiment, the outlet pressure and gas-water production of the second simulated gas well are controlled by controlling the second back-pressure valve 48 and the flow controller 46 of the second simulated gas well to simulate different drainage strengths.

In the embodiment, the specific structure, operation principle and beneficial effect of the physical simulation experimental method for water invasion and drainage gas recovery in gas reservoir have been described in Embodiment 1; and the specific experiment and the experimental method have also been described in Embodiment 1, and will not be repeated herein.

In combination with the actual problem of water invasion and drainage gas recovery in the production process, the physical simulation experimental method for water invasion and drainage gas recovery in gas reservoir according to the invention is established. In consideration of various geological factors and production measures such as reservoir with different physical properties, the scale of different water bodies, different production distribution and the like, an experiment of water invasion into a gas reservoir is carried out to make a study on main controlling factors and the dynamic law of water invasion, to clarify the influence of water invasion on the cutting effect of gas reservoir and the distribution of remaining reserves, and provide basis for the adjustment of development policy and well network deployment. The physical simulation experiment of drainage gas recovery is carried out continuously after water production in gas wells, to simulate and reveal different drainage gas recovery modes, timing, scale and their influence on the recovery ratio of the gas reservoir, and provide theoretical support for preventing unreasonable invasion of edge and bottom water and formulating water control countermeasures. The invention has great significance on studying multiphase seepage, water invasion and water production laws of oil and gas reservoirs, production of remaining reserves, water control countermeasures, and the like.

The foregoings are several embodiments of the present invention, and those skilled in the art may make various modifications or variations to the embodiments of the present invention according to the disclosure of the application documents without departing from the spirit and scope of the present invention.

The invention claimed is:

1. A physical simulation experimental device for a water invasion and drainage gas recovery in a gas reservoir, comprising:
 a heterogeneous reservoir model having a first core holder and a second core holder, wherein an inlet end of the first core holder is connected to an inlet end of the second core holder through an inlet pipeline, an outlet end of the first core holder is connected to an outlet end of the second core holder through an outlet pipeline, a third core holder is connected between a middle portion of the first core holder and a middle portion of the second core holder, and a fourth core holder is connected to the outlet pipeline;
 a gas injection mechanism having a gas injection bottle and a gas injection cylinder connected to the gas injection bottle, wherein the gas injection cylinder is connected to the inlet pipeline; and
 a water body simulation mechanism having a water storage tank and a water injection pump connected to the water storage tank, wherein the water storage tank is connected to the inlet pipeline.

2. The physical simulation experimental device for the water invasion and drainage gas recovery in the gas reservoir according to claim 1, further comprising: a confining pressure mechanism including a confining pressure pump and a plurality of confining pressure pipelines connected to the confining pressure pump, wherein the plurality of confining pressure pipelines are connected to the first core holder, the second core holder, the third core holder, and the fourth core holder, respectively.

3. The physical simulation experimental device for the water invasion and drainage gas recovery in the gas reservoir according to claim 1, further comprising: a pressure testing mechanism having a plurality of pressure sensors, wherein the first core holder, the second core holder, the third core holder, and the fourth core holder are respectively connected with at least one of the pressure sensors.

4. The physical simulation experimental device for the water invasion and drainage gas recovery in the gas reservoir according to claim 1, further comprising: a saturation testing mechanism having a plurality of resistivity probes, wherein the first core holder, the second core holder, the third core holder, and the fourth core holder are respectively connected with at least one of the resistivity probes.

5. The physical simulation experimental device for the water invasion and drainage gas recovery in the gas reservoir according to claim 1, further comprising: at least one gas-water production and metering mechanism connected to the heterogeneous reservoir model, wherein the gas-water production and metering mechanism includes a gas-water separation meter and a flow controller.

6. The physical simulation experimental device for the water invasion and drainage gas recovery in the gas reservoir according to claim 5, wherein the first core holder is connected with the one gas-water production and metering mechanism, the gas-water separation meter of the gas-water production and metering mechanism is connected to an outlet end of the fourth core holder through a first outlet water pipeline on which the flow controller of the gas-water production and metering mechanism and a first back-pressure valve are provided.

7. The physical simulation experimental device for the water invasion and drainage gas recovery in the gas reservoir according to claim 5, wherein the second core holder is connected with another gas-water production and metering mechanism, a gas-water separation meter of the another gas-water production and metering mechanism is connected to the second core holder by a second outlet water pipeline on which a flow controller of the another gas-water production and metering mechanism and a second back-pressure valve are provided.

8. The physical simulation experimental device for the water invasion and drainage gas recovery in the gas reservoir according to claim 1, wherein a first gas injection valve is connected between the gas injection bottle and the gas injection cylinder, and a second gas injection valve is connected between the gas injection cylinder and the inlet pipeline.

9. The physical simulation experimental device for the water invasion and drainage gas recovery in the gas reservoir according to claim 1, wherein a first water injection valve is connected between the water storage tank and the water injection pump, and a second water injection valve is connected between the water storage tank and the inlet pipeline.

10. A physical simulation experimental method for a water invasion and drainage gas recovery in a gas reservoir, wherein the method is applied on the physical simulation experimental device for the water invasion and drainage gas recovery in the gas reservoir according to claim 1, and the physical simulation experimental method for the water invasion and drainage gas recovery in the gas reservoir comprises the following steps of:
- step S1: selecting a fractured rock sample which has a natural fracture or in which an artificial fracture of a rock sample is made, or selecting a matrix rock sample having no fracture, to form an experimental rock sample;
- step S2: putting the experimental rock sample into the first core holder, the second core holder, the third core holder and the fourth core holder, respectively; and
- step S3: starting the gas injection mechanism and the water body simulation mechanism to inject gas and water body into the heterogeneous reservoir model to simulate the gas reservoir environment.

11. The physical simulation experimental method for the water invasion and drainage gas recovery in the gas reservoir according to claim 10, wherein a step S4 is performed after the step S3: the fourth core holder of the heterogeneous reservoir model is connected with a gas-water production and metering mechanism to form a first simulated gas well, the gas-water production and metering mechanism includes a gas-water separation meter and a flow controller; and the gas or water body in the heterogeneous reservoir model is discharged through the gas-water production and metering mechanism to simulate a fracture water invasion process in the gas reservoir.

12. The physical simulation experimental method for the water invasion and drainage gas recovery in the gas reservoir according to claim 11, wherein the experimental rock samples having different permeabilities are placed in the first core holder, the second core holder, the third core holder and the fourth core holder, respectively, to simulate influences of different fracture sizes.

13. The physical simulation experimental method for the water invasion and drainage gas recovery in the gas reservoir according to claim 11, wherein the experimental rock samples having different lengths are placed in the first core holder, the second core holder, the third core holder and the fourth core holder, respectively, to simulate influences of different matrix scales and different degrees of fracture penetration.

14. The physical simulation experimental method for the water invasion and drainage gas recovery in the gas reservoir according to claim 11, wherein the heterogeneous reservoir model is supplemented with water body by the water body simulation mechanism, to simulate influences of different water body sizes.

15. The physical simulation experimental method for the water invasion and drainage gas recovery in the gas reservoir according to claim 11, wherein the gas-water production and metering mechanism of the first simulated gas well is provided with a first back-pressure valve, an outlet pressure and gas flow rate of the first simulated gas well are controlled by the first back-pressure valve and the flow controller, to simulate the influences of different waste pressures and production allocations.

16. The physical simulation experimental method for the water invasion and drainage gas recovery in the gas reservoir according to claim 11, wherein the gas-water production and metering mechanism of the first simulated gas well is provided with a first back-pressure valve; a waste pressure of the heterogeneous reservoir model is set through the first back-pressure valve and then production is performed, the water body in the heterogeneous reservoir model begins to invade into the experimental rock samples, and by adjusting the first back-pressure valve, an outlet pressure of the first simulated gas well is reduced to simulate a process of drainage gas recovery of the first simulated gas well.

17. The physical simulation experimental method for the water invasion and drainage gas recovery in the gas reservoir according to claim 16, wherein the second core holder of the heterogeneous reservoir model is connected with the gas-water production and metering mechanism to form a second simulated gas well, and a process of cooperative drainage gas recovery is simulated though the second simulated gas well and the first simulated gas well.

18. The physical simulation experimental method for the water invasion and drainage gas recovery in the gas reservoir according to claim 17, wherein the gas-water production and metering mechanism of the second simulated gas well is provided with a second back-pressure valve, and an opening timing of the second back-pressure valve is controlled to simulate different drainage timings.

19. The physical simulation experimental method for the water invasion and drainage gas recovery in the gas reservoir according to claim 17, wherein the gas-water production and metering mechanism of the second simulated gas well is capable of connecting to an outlet end of the second core holder or to a side wall of the second core holder to simulate different drainage locations.

20. The physical simulation experimental method for the water invasion and drainage gas recovery in the gas reservoir according to claim 18, wherein an outlet pressure and gas-water production of the second simulated gas well are controlled by controlling the second back-pressure valve and the flow controller of the second simulated gas well to simulate different drainage strengths.

* * * * *